United States Patent

Besemer et al.

[11] Patent Number: 5,879,401
[45] Date of Patent: Mar. 9, 1999

[54] ACETABULAR TRIAL

[75] Inventors: John W. Besemer, Sudbury; Salvatore Caldarise, Hanson, both of Mass.; Frank R. Foley, West Byfleet; Allan Ritchie, New Milton, both of United Kingdom; C. M. Jayashankar, Raynham; Anthony Sanders, Lakeville, both of Mass.

[73] Assignee: Johnson & Johnson Professional, Inc., Raynham, Mass.

[21] Appl. No.: 649,150

[22] Filed: May 17, 1996

[51] Int. Cl.$^6$ .............................. A61F 2/32; A61F 2/30; A61F 2/34; A61F 2/36
[52] U.S. Cl. .................. 623/22; 623/18; 623/23
[58] Field of Search .................. 606/81, 87, 91; 623/18, 22, 23

[56] References Cited

U.S. PATENT DOCUMENTS

| | | | |
|---|---|---|---|
| 4,642,123 | 2/1987 | Noiles | 623/22 |
| 5,320,625 | 6/1994 | Bertin | 606/91 |
| 5,431,657 | 7/1995 | Rohr | 606/91 |
| 5,507,824 | 4/1996 | Lennox | 623/22 |
| 5,571,111 | 11/1996 | Aboczky | 606/91 |

*Primary Examiner*—Michael J. Milano
*Assistant Examiner*—John M. Black
*Attorney, Agent, or Firm*—Susan M. Schmitt

[57] ABSTRACT

An acetabular trial insert is provided in which the appropriate anteversion angle of the acetabular cup of a hip prosthesis may be determined automatically by placing an inner cup within an outer cup and providing a mechanism which will hold the inner cup in position after the trial has been reduced and the hip rotated through an intended range of motion.

21 Claims, 6 Drawing Sheets

ACETABULAR TRIAL

FIELD OF THE INVENTION

The present invention relates to an acetabular trial for accurately determining the appropriate placement angles to optimally orient an acetabular cup component of a hip prosthesis in hip replacement surgery.

BACKGROUND OF THE INVENTION

Placement of the acetabular cup in a hip replacement surgery is critical to providing a securement of the femoral portion as well as in providing an optimal range of motion for the patient. If the acetabular cup is improperly placed it can result in a limited range of motion or dislocation.

Typically the hip socket or acetabulum of a patient lies 35° to 45° of the midsagittal plane and is rotated forward 15° to 20° off the coronal plane. In hip replacement surgery usually, the cup implant is oriented in the acetabulum by using an acetabular cup positioning instrument. This instrument includes a horizontal arm that will align parallel to the long axis of a patient at a preferred abduction angle, i.e., 40°, and is therefore dependent upon the correct positioning of the patient. The cup placement is typically done by visually adjusting the cup to ensure that the horizontal arm of the device is approximately parallel to the long axis of the patient. This is done independent of femoral stem implant placement.

Once the abduction angle is set, the anteversion is then set by rotating the alignment device forward and then ensuring that a second arm on the cup positioner at a preset angle (typically about 20°) is aligned parallel to the long axis of the patient thus selecting a predetermined or standard anteversion angle.

This method is dependent upon correct positioning of the patient and also uses "eyeballing" to position the cup at a preset angle while not taking into consideration the variations from individual to individual. This method also does not take into consideration the acetabular cup interaction with the femoral component which is important for optimizing the range of motion for an individual.

Accordingly, one object of the invention is to provide an acetabular trial that would assist in the determination of optimal positioning of the cup for the best and most normal range of motion, and for a securedly placed acetabular cup. Another object of the invention is to take into consideration the acetabular cup interaction with the femoral component is setting the acetabular cup alignment.

SUMMARY OF THE INVENTION

The present invention provides a trial system comprised of at least two working parts, an inner bearing and an outer shell. The outer shell is attached to the acetabulum preferably at a predetermined angle or in a referenced or referenceable position while the inner bearing within the outer shell is allowed to move in a limited manner to set the placement angle.

The present invention maximizes the available range of motion by allowing movement of the bearing when a force is applied to it. When the hip is reduced and an impingement of the neck of the prosthetic femoral trial occurs with the edge of the inner cup during flexion or extension of the hip, the bearing position will adjust accordingly. By putting the limb through extreme ranges of flexion/extension and abduction/adduction, one can produce the final optimal position of the inner bearing.

In one preferred embodiment, the outer shell is attached to the acetabulum at approximately a 40° abduction angle while the inner bearing within the outer shell is allowed to move in a limited manner to set the anteversion angle.

In a preferred embodiment, a spring-loaded ratchet system permits incremental angular movement in either direction off the coronal plane about the medial-lateral anteversion axis, to produce the appropriate anteversion angle. From the movement of the inner bearing which results from impingement with the prosthetic femoral stem, particularly the prosthesis neck, during trial reduction with the trial femoral head, the appropriate anteversion angle is identified for the greatest range of motion. The trial joint is then dislocated and the resulting position of the trial is replicated with an actual component.

In one preferred embodiment, the device comprises three mating bearings wherein the outermost bearing or shell may be selected from a plurality of outer shells having various outer diameters, thus allowing the surgeon to select and trial a number of cup sizes.

In this embodiment, the inner bearing includes a centrally located hole for receiving a reference pin which is passed through the hole, through openings in the outer bearings and into the underlying bone. The pin is left in the bone when the trial cup is removed, establishing a reference for implanting a prosthetic cup when the trial cup is removed.

DETAILED DESCRIPTION OF THE DRAWINGS

DETAILED DESCRIPTION OF THE INVENTION

Figure 1:
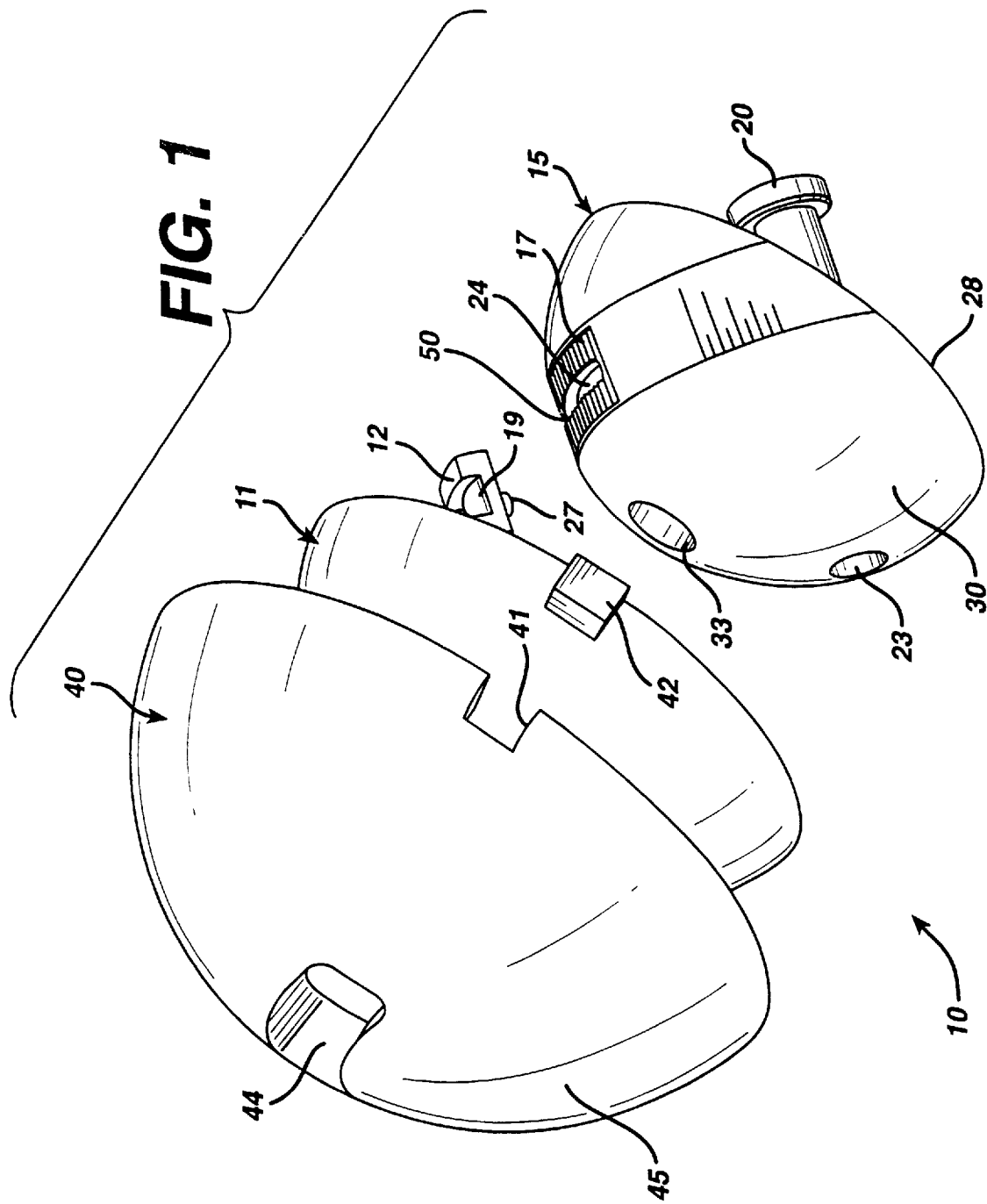
FIG. 1 illustrates an exploded perspective view of the trial of the present invention from an antero-medial view.
Figure 2:
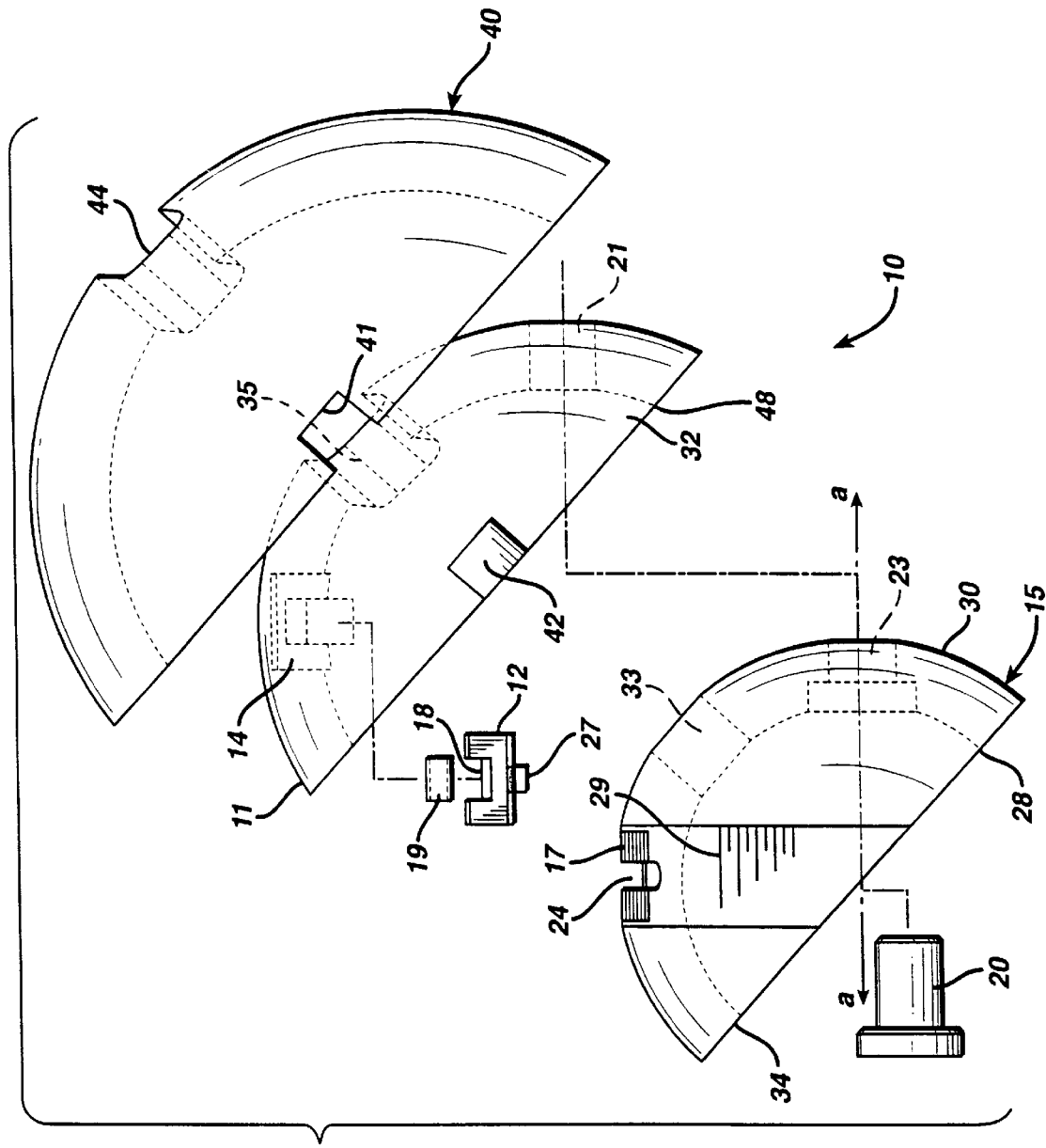
FIG. 2 illustrates a cross-section of the trial of FIG. 1.
Figure 3:
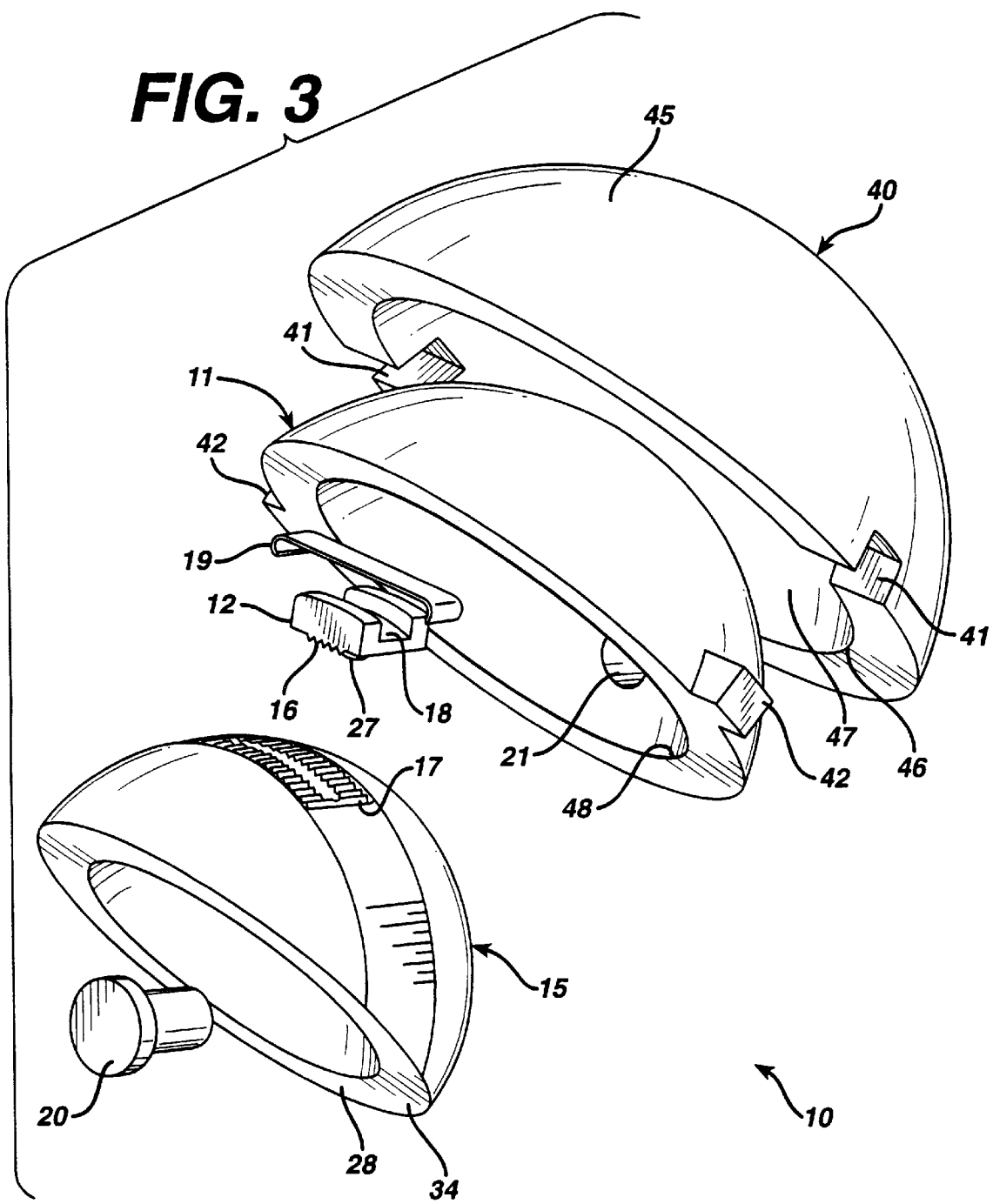
FIG. 3 illustrates an exploded perspective view from the anterior side of the trial of the present invention.
Figure 4:
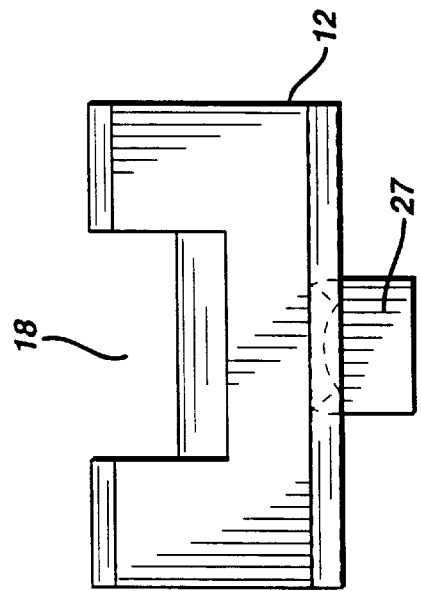
FIG. 4 illustrates a side view of pawl insert of the trial of FIG. 1.
Figure 5:
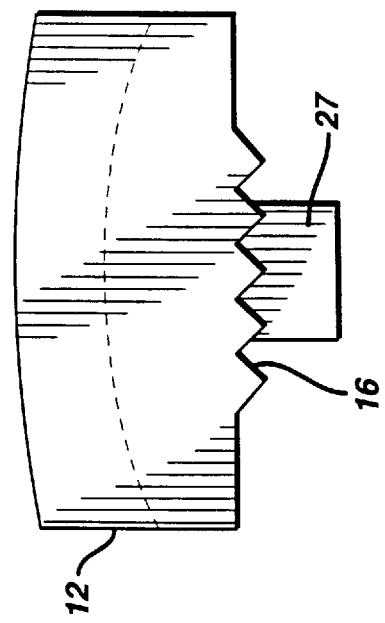
FIG. 5 illustrates a front view of the pawl insert of the trial of FIG. 1.
Figure 6:
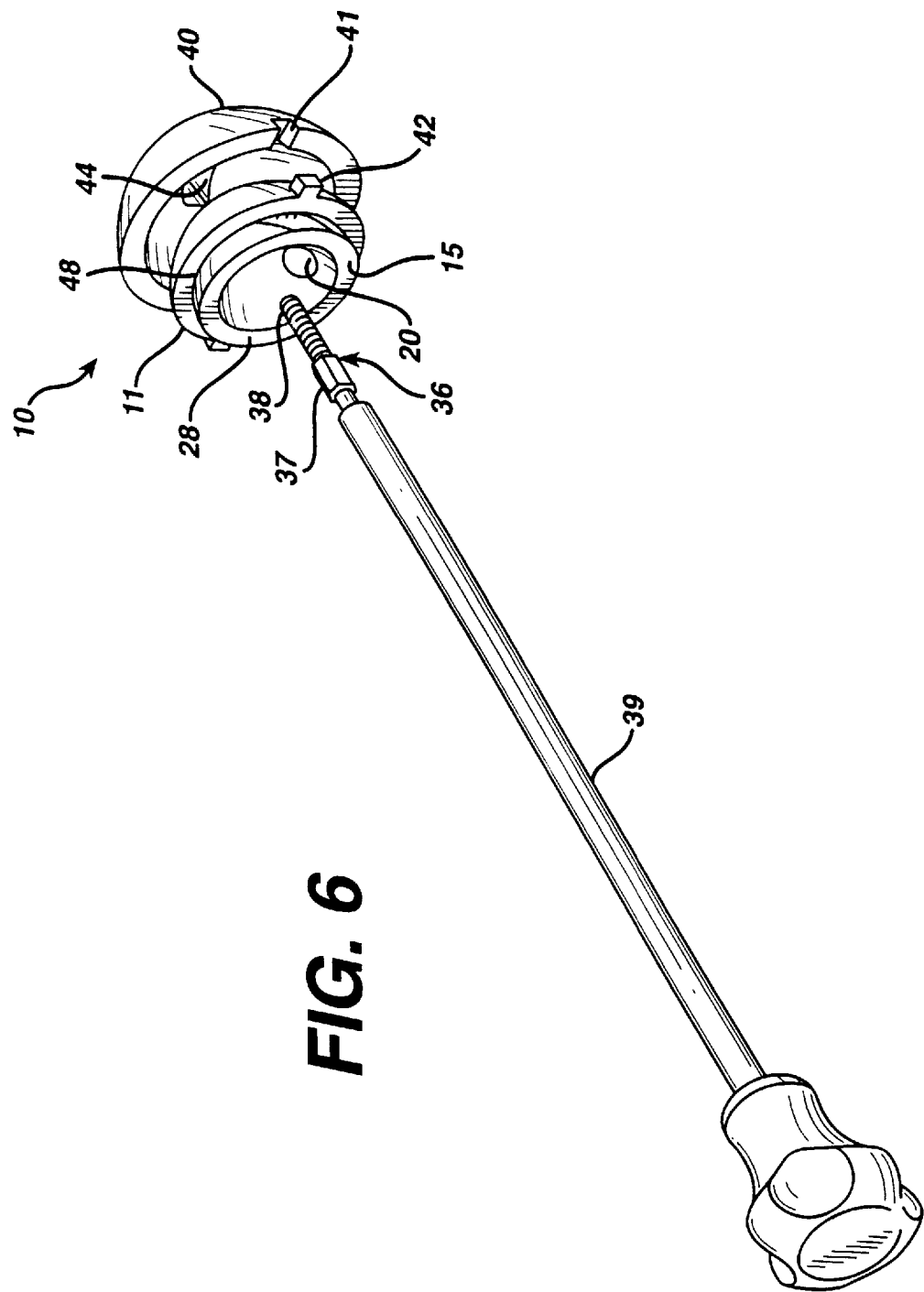
FIG. 6 illustrates an exploded perspective view of the trial cup of FIG. 1 with a reference pin inserting instrument.

Referring now to FIGS. 1 through 6 there is illustrated a acetabular trial system 10 of the present invention, comprising inner cup or bearing 15, an outer bearing or middle cup 11 and an outer augmentation shell 40. The augmentation shell 40 comprises an outer spherical surface 45 to interface with a patient's acetabulum, a distal opening 46 forming an inner spherical surface 47 for receiving the outer bearing 11 of the trial 10, a slot 44 in top of the shell 40 for receiving a reference pin therethrough, and slots 41 for receiving tabs 42 on the outer bearing 11.

Preferably, a plurality of augmentation shells 40 are used having multiple diameters, typically from about 40 mm to about 70 mm, to accommodate the various patient acetabula sizes. The inner diameter is uniform for each of the shells so that each closely fits with the outer diameter of the outer bearing 11, thus allowing use of the same outer and inner bearings 11, 15 with each of the various sized shells. Also, preferably, a plurality of inner bearings 15 have a variety of inner diameter sizes to accomodate a variety of head sizes, thereby permitting the surgeon flexibility in selecting a desireable head size for the femoral component of an implant.

The augmentation shell 40 may include pins (not shown) extending in a superior-medial direction from the shell 40. The pins (not shown) are used to temporarily fix the shell 40 into the acetabulum of a patient at an abduction angle generally at about 40°.

The outer bearing 11 comprises an opening 21 for receiving a pin 20 for rotatably attaching an inner bearing 15 inside the outer bearing 11. The outer bearing 11 further includes a recess 14 for receiving a spring-loaded pawl insert 12.

The pawl insert 12 includes teeth 16 for engaging the serrations 17 on the outer surface of the inner bearing 15 and a recess 18 for receiving leaf spring 19 which biases the pawl 12 in a direction towards the inner bearing 15.

The outer bearing 11 also includes a slot 35 in the top which serves as an aperture into which a reference screw 36 may be inserted through the trial 10 into the acetabulum bone.

The inner bearing 15 comprises a hole 33 having an axis perpendicular the plane of the rim 34 of the inner bearing. The hole 33 of the inner bearing 15 is always contained within the extents of the slot 35 of the outer bearing 11 and the slot 44 of the shell 40 throughout the entire range of motion of the inner bearing with respect to outer bearing 11 and shell 40.

The inner bearing 15 comprises an opening 23 for receiving pin 20. The opening 23 is aligned with the opening 21 of the outer bearing 11 when pin 20 is inserted through openings 23, 21. The pin 20 permits the inner bearing 15 to rotate about the axis a of the pin 20, with respect to outer bearing 11. The inner bearing 15 further comprises serrations 17 which are located on the outer surface 30 of the inner bearing at a 90° angle from the opening 23, i.e., the axis 9 of the pin 20. A groove 24 is formed in the outer surface 30 of the inner bearing 15 through the serrations 17. The groove 24 extends 20° on each side of a middle point 50 within the groove 24. The middle point 50 is defined by the plane of symmetry of the device. A tab 27 located on the pawl 12 fits within groove 24 and permits rotation of the inner bearing 15 about pin 20 for 20° on either side of the middle point 50 of the groove 24. The spring 19 biases the pawl 12 in a direction towards the serrations 17 causing the teeth 16 of the pawl 12 to engage with the serrations 17. The serrations 17 are spaced in preset angular increments preferably of about 2.5°.

In use, an appropriate size shell 40 is selected and fitted into the acetabulum of a patient who is to receive an artificial hip implant including an acetabular cup. The pins 22 are used to temporarily fix the outer shell 40 to the acetabulum at a 40° abduction angle.

The inner bearing 15 as assembled is inserted into the outer bearing 11 such that the opening 23 of the inner bearing 15 is aligned with the opening 21 of the outer bearing 11 and so that the tab 27 of the pawl 12 is located within the groove 24 on the outer surface of the inner bearing 15. As assembled, the pin 20 is inserted through openings 23 and 21 to rotatably fix the inner bearing 15 to the outer bearing 11. The horizontal axis of the pin 20 defines an axis of rotation of the anteversion angle.

The assembly of the outer and inner bearing 11, 15 is inserted into the shell opening 46 forming the inner arcuate or spherical surface 47. The tabs 42 of the outer bearing 11 fit into slots 41 within the augmentation shell 40, thus aligning and holding itself within the augmentation shell 40.

Figure 7:
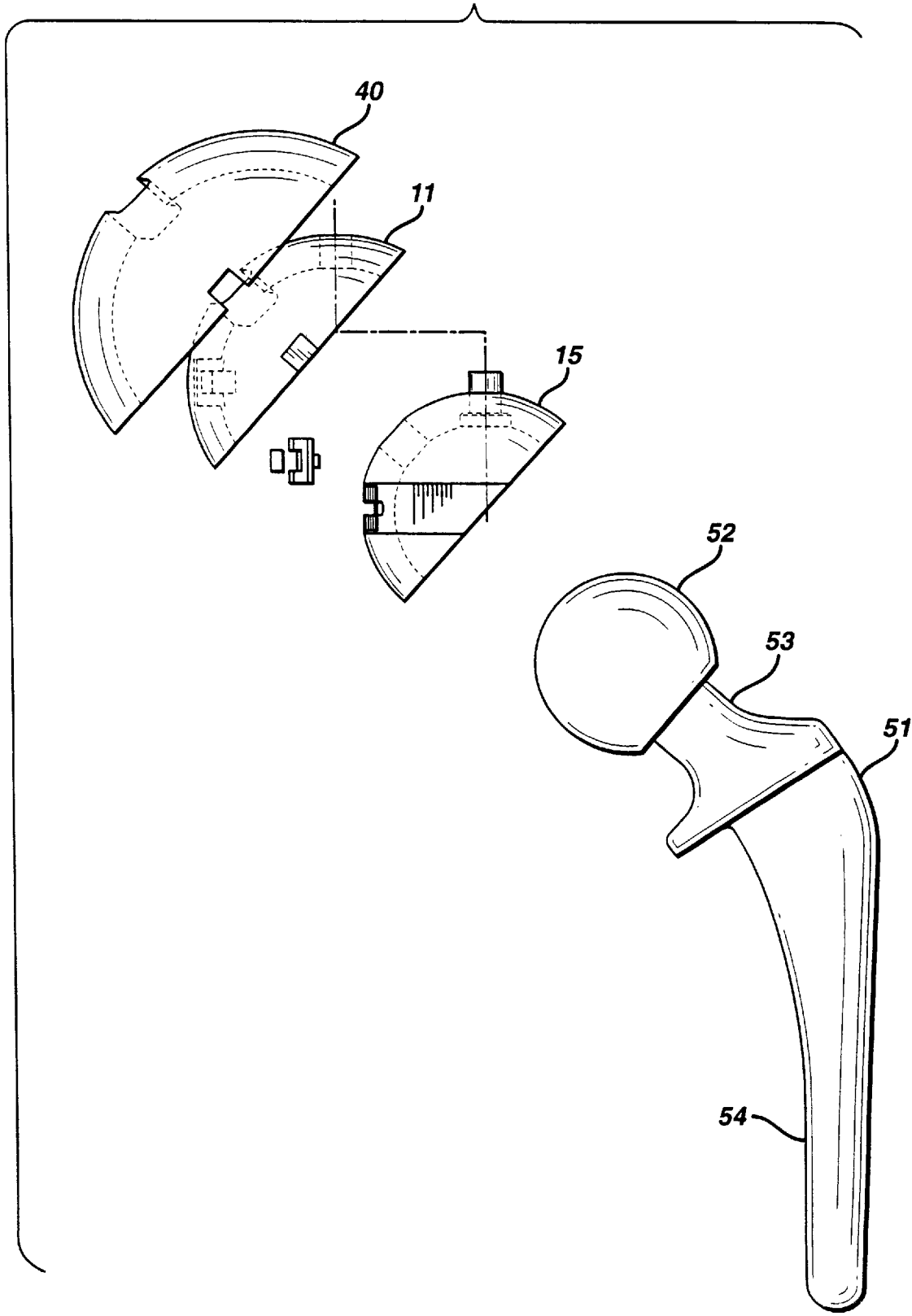
FIG. 7 illustrates a cross-section of the trial of FIG. 1 with a femoral component.

Referring now to FIG. 7 a femoral component 51 is illustrated in use with the acetabular trial sytem 10. The femoral component 51 comprises a head portion 52 comprising a convex spherical surface for articulating within the inner bearing or cup 15. The head portion 52 is coupled to a neck 53 which is then coupled to a shank portion 54 to be placed within a femoral cavity of a pateint's hip. The femoral component is most preferably a femoral trial, although the actual femoral component implant may be used as the femoral component with the acetabular trial system 10. The neck 53 is preferably a separate piece to be assembled with the head portion 52 and shank portion 54. The shank portion 54 may be a broach used to remove bone material within the femoral cavity or may be a stem trial or the stem of femoral component implant. The trial or implant or trial may be for a cemented type implant or a press-fit type implant.

In use, the femoral component 51 is placed in a prepared femoral cavity of a patient's hip and the head 52 of the femoral component 51 is inserted into the inner bearing 15 and the joint is reduced. The femoral component 51 may then be rotated to an extreme in all directions with respect to the acetabular trial 10 by rotating, extending, flexing, adducting and abducting the hip joint. In doing so the range of motion of the hip is imitated.

If the neck 53 of the femoral component 51 contacts the edge 28 of the inner bearing 15 at such points on the edge 28 that the contact force creates a torque which is substantially about the axis of the pin 20, then the inner bearing 15 will rotate. However, because of the pawl 12 contacting the serrations 17 of the inner bearing 15, some resistance will be felt by the surgeon and an auditory feedback will be caused by the movement of the pawl 12 over the serrations 17. This rotation is limited by a stop mechanism, i.e., the tab 27 of the pawl 12 hitting the end of the groove 24, 20° in either direction of the middle point 50 of the groove 24. Thus, after the inner bearing 15 is rotated, the pawl 12 will hold the inner bearing in place.

If the trial 10 is removed, the inner bearing 15 will show the appropriate anteversion angle or position for setting the ultimate desired acetabular cup implant position. Indicating lines 29 will show the appropriate anteversion angle at the point that such line abuts the edge 48 of the rim 32 of the outer bearing 11. Also, once the anteversion angle is set using this technique, the reference screw 36 is inserted into the bone through inner bearing hole 33, and slots 35, 44 in outer bearing 11 and shell 40 respectively. The reference screw 36 comprises a hexagonal socket head 37 and threads 38. A screw insertion rod 39 (FIG. 6) is used to insert the screw through hole 33 and slots 35, 44 and drive it into the underlying acetabulum bone. The insertion rod 39 is then removed from the screw 36 and the trial 10 is removed from the acetabulum, leaving the screw 36 in place as a reference for cup implant placement.

The acetabular cup implant is placed over the head 37 of the reference screw 36. Thus, the acetabular cup implant is oriented and positioned just as the trial 10 had been. In the case of a cemented implant, an addition trial having an apical central hole may be used to demarcate the desired position. The trial is inserted over the rod or pin 39 and the location of the trial is marked. The cemnted implant may then be inserted and aligned with the marks. This is necessary due to the fact that the cemented cup preferably should not have a central hole.

The desired angle may also be verified upon remaoval of the trial 10 from the acetabulum with the indicating lines 29 as described above. Finally, using the insertion rod 39, the reference screw 36 is removed through the acetabular cup implant's apical hole, without disturbing the placement of the cup.

In an alternative embodiment, bearings 11, 15 may be used alone with the outer bearing acting as an interface with the acetabulum. In such embodiment the outer bearing 11 acts as the outer shell and is fixed into place in the acetabulum using pins in a similar manner as described above with respect to the shell 40.

Although the present invention is described with respect to a particular embodiment it will be apparent to those skilled in the art that various modifications may be made without departing from the character and scope of the invention. For example, the abduction angle may be set using the same device by placing the fixation pin in a position where it will allow the inner cup to rotate about the anterior-posterior axis. Also, alternatively, the longitudinal axis as opposed to transverse axis may be used for setting the anteversion angle. It may also be desirable to orient the hip about a different axis to optimize hip placement. In each of such circumstances, the two cup system and method as described and claimed herein may be used.

What is claimed is:

1. An acetabular trial system for use in prosthetic hip implantation Surgery, said system comprising:

an outer shell for placement on an acetabulum of a patient;

an inner cup for placement within said outer shell; and a fixation device to rotatably fix said inner cup within said outer shell to permit said inner cup to rotate about a selected axis wherein said selected axis is a transverse axis extending through said outer shell and defining a range of anteversion angles, said transverse axis being perpendicular to a sagittal plane of a patient's body.

2. The system of claim 1 further comprising:

a restriction device engaging said inner cup with said outer shell to restrict the rotation of said inner cup about said selected axis.

3. The trial system of claim 2 wherein said restriction device further comprising a spring-loaded ratchet for incrementally permitting rotation of said inner cup about said selected axis.

4. The trial system of claim 1, further comprising an anteversion angle indicator located on said inner cup.

5. The trial system of claim 1 further comprising a reference pin;

wherein said outer shell and inner cup each comprise an opening for receiving said pin wherein said openings are aligned so that said pin may be passed therethrough and into the bone of an acetabulum into which said outer shell is inserted.

6. The trial system of claim 1 further comprising a reference pin;

wherein said outer shell and inner cup each comprise an opening for receiving said pin wherein said openings are aligned so that said pin may be passed therethrough and into the bone of an acetabulum into which said outer shell is inserted;

wherein said inner shell is rotatable about a selected axis defining a range of cup placement angles with respect to said selected axis; and wherein said openings align throughout said range so that said reference pin may be inserted through said openings throughout said range.

7. An acetabular trial system for use in prosthetic hip implantation Surgery, said system comprising:

an outer shell for placement on an acetabulum of a patient;

an inner cup for placement within said outer shell; and a fixation device to rotatably fix said inner cup within said outer shell to permit said inner cup to rotate about a selected axis;

said trail systems further comprising a plurality of inner cups having a plurality of inner cup diameters; wherein one of said inner cups having a preferred diameter may be selected from said plurality of inner cups for a hip trial reduction.

8. An acetabular trial system for use in prosthetic hip implantation Surgery, said system comprising:

an outer shell for placement on an acetabulum of a patient;

an inner cup for placement within said outer shell; and a fixation device to rotatably fix said inner cup within said outer shell to permit said inner cup to rotate about a selected axis;

said trial system further comprising:

a middle cup positionable within said outer shell between said outer shell and said inner cup, said middle cup having an outer diameter;

wherein said outer shell has an inner diameter, said outer diameter of said middle cup fitting within said inner diameter of said outer shell; and wherein said fixation device rotatably couples said inner cup with said middle cup to permit said inner cup to rotate with respect to said middle cup.

9. The trial system of claim 8 further comprising:

a plurality of said outer shells having a plurality of outer diameters, wherein said inner diameters of each of said outer shells uniform in size with respect to the inner diameter of each of the other of said plurality of outer shells.

10. The trial system of claim 8 further comprising a reference pin wherein said outer shell, middle cup and inner cup each comprise an opening for receiving said pin; wherein each said opening is aligned with the other said openings so that said pin may be passed therethrough and into bone of an acetabulum in which said outer shell is placed.

11. The trial system of claim 10 wherein said inner cup is orientable about a transverse axis defining a range of anteversion angles; and wherein said openings in said middle cup and outer shell permit movement with respect to said pin of said middle cup and said outer shell throughout said range of angles.

12. The trial system of claim 8 comprising a plurality of inner cups having a plurality of inner cup diameters; wherein one of said inner cups having a preferred diameter may be selected from said plurality of inner cups for a hip trial reduction.

13. An acetabular trial system for use in prosthetic hip implantation Surgery, said system comprising:

an outer shell for placement on an acetabulum of a patient;

an inner cup for placement within said outer shell; and a fixation device to rotatably fix said inner cup within said outer shell to permit said inner cup to rotate about a selected axis wherein said selected axis is a longitudinal axis of a patient's body.

14. A method for determining an acetabular cup placement position comprising:

providing an acetabular trial comprising:

an outer shell for placement on an acetabulum of a patient;

an inner cup for placement within said outer shell;
a fixation device to rotatably fix said inner cup within said outer shell to permit said inner cup to rotate about a selected axis;
placing the trial in the acetabulum of a patient's limb at a selected position;
fixing the outer shell in said selected position;
inserting a femoral component in a prepared femoral bone cavity of the patient's limb, said femoral component comprising:
a shank portion for inserting into a femoral cavity; a neck portion coupled to said shank portion; and a head coupled to said neck portion;
placing the head of the femoral component in the inner cup of the acetabular trial;
moving the limb through a range of motion, that causes the neck of the femoral component to impinge on the inner cup to rotate the inner cup with respect to the outer shell into a trial orientation; and
determining a preferred cup implant position based on the trial orientation.

15. The method of claim 14 further comprising:
providing a middle cup positionable within said outer shell between said outer shell and said inner cup, said middle cup having an outer diameter;
wherein said outer shell has an inner diameter, said outer diameter of said middle cup fitting within said inner diameter of said outer shell; and
wherein said fixation device rotatably couples said inner cup with said middle cup to permit said inner cup to rotate with respect to said middle cup.

16. The method of claim 15 further comprising:
providing a plurality of said outer shells having a plurality of outer diameter sizes, wherein said inner diameter of each of said outer shells is uniform in size with respect to the inner diameter of each of the other of said plurality of outer shells;
selecting a preferred outer shell of a preferred diameter prior to placing said trial on said acetabulum; and
placing said inner cup and middle cup within said inner diameter of said preferred outer shell to provide a said trial.

17. The method of claim 14 further comprising:
providing a plurality of inner cups having a plurality of different inner diameters, selecting a preferred inner cup of a preferred inner diameter; and
placing said preferred inner cup and middle cup within said inner diameter of said outer shell to provide a said trial.

18. A method for aligning an acetabular cup implant comprising:
providing an acetabular trial comprising:
an outer shell for placement on an acetabulum of a patient, said outer shell comprising an apical opening;
an inner cup for placement within said outer shell, said inner cup comprising an apical opening;
a fixation device to rotatably fix said inner cup within said outer shell to permit said inner cup to rotate about a selected axis;
a stop coupled to said inner cup for limiting rotation of said inner cup about said selected axis to a range of orientation angles of said inner cup with respect to said outer cup, wherein said apical opening of said inner cup is aligned with at least a portion of the apical opening of said outer shell throughout said range of angles to permit the insertion of said pin therethrough; and
a pin for inserting through said apical openings of said inner cup and said outer shell;
placing the trial in the acetabulum of a patient's limb at a selected reference position;
fixing the outer shell in said selected reference position;
inserting a femoral component in a prepared femoral bone cavity of the patient's limb, said femoral component comprising:
a shank portion for inserting into a femoral cavity; a neck portion coupled to said shank portion; and a head coupled to said neck portion;
placing the head of the femoral component in the inner cup of the acetabular trial;
moving the limb through a range of motion, that causes the neck of the femoral component to impinge on the inner cup to rotate the inner cup with respect to the outer shell, within said range of angles, into a preferred trial orientation of said inner cup;
inserting said pin through said apical opening of said inner cup and said apical opening of said outer shell into underlying acetabulum of said patients limb to reference said orientation of said inner cup with placement of the pin;
removing said acetabular trial; and
using the placement of the pin to place an acetabular cup implant in a position having the preferred trial orientation of the inner cup.

19. The method of claim 18 further comprising:
providing a middle cup positionable within said outer shell between said outer shell and said inner cup, said middle cup having an outer diameter and an apical opening;
wherein said apical opening of said inner cup is aligned with at least a portion of the apical opening of said middle cup throughout said range of angles to permit the insertion of said pin therethrough;
wherein said outer shell has an inner diameter, said outer diameter of said middle cup fitting within said inner diameter of said outer shell; and
wherein said fixation device rotatably couples said inner cup with said middle cup to permit said inner cup to rotate with respect to said middle cup.

20. The method of claim 19 further comprising:
providing a plurality of said outer shells having a plurality of outer diameter sizes, wherein said inner diameter of each of said outer shells is uniform in size with respect to the inner diameter of each of the other of said plurality of outer shells;
selecting a preferred outer shell of a preferred diameter prior to placing said trial on said acetabulum; and
placing said inner cup and middle cup within said inner diameter of said preferred outer shell to provide a said trial.

21. The method of claim 18 further comprising:
providing a plurality of said inner cups having a plurality of inner diameter sizes,
selecting a preferred inner cup of a preferred inner diameter; and
placing said preferred inner cup an middle cup within said inner diameter of said outer shell to provide a said trial.

* * * * *